United States Patent [19]

Paessens et al.

[11] Patent Number: 4,668,660

[45] Date of Patent: * May 26, 1987

[54] ANTIVIRAL AGENTS

[75] Inventors: Arnold Paessens, Haan; Gert Streissle, Wuppertal; Manfred Plempel, Haan; Karl H. Büchel, Burscheid; Hans-Ludwig Elbe; Graham Holmwood, both of Wuppertal; Udo Kraatz, Leverkusen; Erik Regel, Wuppertal, all of Fed. Rep. of Germany

[73] Assignee: Bayer Aktiengesellschaft, Leverkusen, Fed. Rep. of Germany

[*] Notice: The portion of the term of this patent subsequent to Jan. 14, 2003 has been disclaimed.

[21] Appl. No.: 598,560

[22] Filed: Apr. 10, 1984

[30] Foreign Application Priority Data

Apr. 30, 1983 [DE] Fed. Rep. of Germany ....... 3315808

[51] Int. Cl.[4] .................. A61K 31/41; A61K 31/415

[52] U.S. Cl. .................. 514/383; 514/397; 514/399

[58] Field of Search .............. 514/383, 397, 399

[56] References Cited

U.S. PATENT DOCUMENTS

| 4,086,351 | 4/1978 | Balasubramanyan et al. ..... 548/262 |
| 4,564,622 | 1/1986 | Streissle et al. ..................... 514/383 |

FOREIGN PATENT DOCUMENTS

| 0040345 | 11/1981 | European Pat. Off. ............ 548/262 |
| 3018865 | 11/1981 | European Pat. Off. ............ 548/262 |

Primary Examiner—Richard L. Raymond
Attorney, Agent, or Firm—Sprung Horn Kramer & Woods

[57] ABSTRACT

The invention relates to hydroxyethylazolyl derivatives, defined herein by formula (I) and particularly to the use of said derivatives for the treatment of viral infections.

8 Claims, No Drawings

ANTIVIRAL AGENTS

The present invention relates to antiviral agents which contain, as the active compounds, hydroxyethyl-azolyl derivatives.

It has been found that the hydroxyethyl-azolyl derivatives of the formula

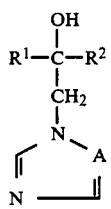

(I)

in which
A represents a nitrogen atom or the CH group,
R¹ represents phenyl, phenoxymethyl, phenethyl or phenethenyl, each of which is optionally substituted in the phenyl moiety, or represents naphthyloxymethyl, 1,2,4-triazol-1-yl-methyl or imidazol-1-yl-methyl,
R² represents the group —C(CH₃)₂—R³, 1,2,4-triazol-1-yl-methyl or imidazol-1-yl-methyl and
R³ represents methyl; and phenoxy or benzyl, both of which are optionally substituted,
with the proviso that A does not represent a nitrogen atom at the same time as R¹ represents p-chlorophenoxymethyl and R² represents tert.-butyl,
and their physiologically tolerated acid addition salts, have potent antiviral effects.

Surprisingly, the hydroxyethyl-azolyl derivatives of the formula (I) show a better antiviral efficacy than the compounds having antiviral activity known from the Chemotherapy of Virus Diseases, Vol. I, p. 115–179 (1972).

The hydroxyethyl-azolyl derivatives to be used according to the invention are generally defined by the formula (I). In this formula
A preferably represents a nitrogen atom or the CH group;
R¹ preferably represents phenyl, phenoxymethyl, phenethyl or phenethenyl, each of which optionally has one, two or three identical or different substituents in the phenyl moiety, such as halogen, alkyl having 1 to 4 carbon atoms, alkoxy and alkylthio, each having 1 or 2 carbon atoms, halogenoalkyl, halogenoalkoxy or halogenoalkylthio, (especially perhalogenoalkyl, perhalogenoalkoxy or perhalogenoalkylthio) each having 1 or 2 carbon atoms with 1 to 5 identical or different halogen atoms, such as fluorine and chlorine atoms, phenyl and halogenophenyl; and furthermore preferably represents naphthyloxymethyl, 1,2,4-triazol-1-yl-methyl or imidazol-1-yl-methyl;
R² preferably represents the group —C(CH₃)₂—R³, or preferably represents 1,2,4-triazol-1-yl-methyl or imidazol-1-yl-methyl; and
R³ preferably represents methyl and preferably represents phenoxy or benzyl, both of which optionally have one, two or three identical or different substituents, suitable substituents preferably being the phenyl substituents mentioned above as being preferred for R¹;
with the proviso that A does not represent a nitrogen atom at the same time as R¹ represents p-chlorophenoxymethyl and R² represents tert.-butyl.

Those compounds of the formula (I) are particularly preferred in which
(A)
R¹ represents phenoxymethyl, phenethyl or phenethenyl, each of which optionally has 1, 2 or 3 identical or different substituents in the phenyl moiety, such as fluorine, chlorine, methyl, trifluoromethyl, trifluoromethoxy, trifluoromethylthio, phenyl and chlorophenyl; or represents naphthyloxymethyl; and
R² represents tert.-butyl, while at the same time A does not represents a nitrogen atom and R¹ does not represent p-chlorophenoxymethyl;
(B)
R¹ represents phenoxymethyl which optionally has one or two identical or different substituents in the phenyl moiety, suitable substituents being the phenyl substituents already mentioned under A; and
R² represents the group —C(CH₃)₂—R³, while
R³ represents phenoxy which optionally has one or two identical or different substituents, suitable substituents being the phenyl substituents already mentioned under A for R¹;
(C)
R¹ represents phenyl which optionally has one or two identical or different substituents, suitable substituents being the phenyl substituents already mentioned under point A; and
R² represents the group —C(CH₃)₂—R³, while
R³ represents phenoxy which optionally has one or two identical or different substituents, suitable substituents being the phenyl substituents already mentioned under A for R¹;
(D)
R¹ represents phenoxymethyl which optionally has one or two identical or different substituents in the phenyl moiety, suitable substituents being the phenyl substituents already mentioned under A; and
R² represents 1,2,4-triazol-1-yl-methyl or imidazol-1-ylmethyl;
(E)
R¹ represents 1,2,4-triazol-1-yl-methyl or imidazol-1-yl-methyl; and
R² represents the group —C(CH₃)₂—R³, while
R³ represents benzyl which optionally has one or two identical or different substituents, suitable phenyl substituents being the phenyl substituents already mentioned under A for R¹.

Additional preferred compounds according to the invention are addition products of acids and those hydroxyethylazolyl derivatives of the formula (I) in which the substituents A, R¹ and R² have the meanings which have already been mentioned as being preferred for these substituents.

The acids which can be added preferably include hydrogen halide acids, such as, for example, hydrochloric acid and hydrobromic acid, especially hydrochloric acid, but also phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and naphthalene-1,5-disulphonic acid. These acids provide, particularly, pharmaceutically acceptable acid-addition-salts.

The active compounds to be used according to the invention are known (compare South African Pat. No. 81-3252, corresponding to U.S. patent application Ser. No. 260,479 and U.S. patent application Ser. No. 256,741, or our own earlier patent applications which have not yet been published deal with them (compare the U.S. patent application Ser. Nos. 456,458; 476,096 and 522,423) and can be obtained by the processes indicated in these texts by, for example, reacting oxiranes of the formula

in which $R^1$ and $R^2$ have the meanings indicated above, with azoles of the formula

in which
A has the meaning indicated above and
B represents hydrogen or an alkali metal, such as sodium or potassium,
in the presence of an inert organic solvent, such as, for example, an alcohol, and optionally in the presence of a base, such as, for example, sodium alcoholate, optionally under a pressure of 1 to 25 bar, at temperatures, between 60° and 150° C.

The acid addition salts of the compounds of the formula (I) can be obtained in a simple manner by customary methods of salt formation, for example by dissolving a compound of the formula (I) in a suitable inert solvent and adding the acid, for example hydrochloric acid, and can be isolated in a known manner, for example by filtering off, and purified, if necessary, by washing with an inert organic solvent.

The compounds of the formula (I) according to the invention have, as already mentioned, potent antiviral effects. These effects are particularly pronounced with viruses which contain lipids, such as, for example, herpes viruses, and for viruses which do not contain lipids, such as, for example, papilloma viruses.

Examples of indications in human medicine which can be mentioned for herpes virus infections are: Herpes labiales, herpes genitalis, keratoconjunctivitis herpetica, varicella (chicken-pox), herpes zoster (shingles), mononucleosis and infections with cytomegalovirus.

Indications in veterinary medicine which can be listed for herpes virus infections are: infections with pseudorabies virus (cattle, pigs), rhinotracheitis virus (cattle), rhinopneumonitis virus (horses) and Marek virus (poultry).

Indications in medicine which may be known for papilloma virus infections are virus-induced warts.

The present invention includes pharmaceutical preparations which in addition to non-toxic, inert pharmaceutically suitable excipients contain one or more active compounds according to the invention or which consist of one or more active compounds according to the invention, and processes for the production of these preparations.

The present invention also includes pharmaceutical preparations in dosage units. This means that the preparations are in the form of individual parts, for example tablets, coated tablets, capsules, bottles, suppositories and ampoules, in which the content of active compound corresponds to a fraction or a multiple of an individual dose. The dosage unit can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

By non-toxic, inert pharmaceutically suitable excipients, there are to be understood solid, semi-solid or liquid diluents, fillers and formulation auxiliaries of all kinds.

Tablets, coated tablets, capsules, pills, granules, suppositories, solutions, suspensions and emulsions, pastes, ointments, gels, creams, lotions, powders and sprays may be mentioned as preferred pharmaceutical preparations.

Tablets, coated tablets, capsules, pills and granules can contain the active compound or compounds alongside the customary excipients such as (a) fillers and extenders, for example starches, lactose, sucrose, glucose, mannitol and silica, (b) binders, for example carboxymethylcellulose, alginates, gelatin and polyvinylpyrrolidone, (c) humectants, for example glycerol, (d) disintegrants, for example agar-agar, calcium carbonate and sodium bicarbonate, (e) solution retarders, for example paraffin and (f) absorption accelerators, for example quaternary ammonium compounds, (g) wetting agents, for example cetyl alcohol, or glycerol monostearate, (h) adsorbents, for example kaolin and bentonite and (i) lubricants, for example talc, calcium stearate and magnesium stearate and solid polyethylene glycols or mixtures of the substances listed under (a) to (i).

The tablets, coated tablets, capsules, pills and granules can be provided with the customary coatings and shells, optionally containing opacifying agents and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a micro-encapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid) or mixtures of these substances.

Ointments, pastes, creams and gels can contain the customary excipients in addition to the active compound or compounds, for example animal and vegetable fats, waxes, paraffins, starch, tragacanth, cellulose derivatives, polyethylene glycols, silicones, bentonites, silica, talc and zinc oxide or mixtures of these substances.

Powders and sprays can contain the customary excipients in addition to the active compound or compounds, for example lactose, talc, silica, aluminium hydroxide, calcium silicate and polyamide powders or mixtures of these substances. Sprays can additionally contain the customary propellants, for example chlorofluorohydrocarbons.

Solutions and emulsions can contain the customary excipients in addition to the active compound or compounds, such as solvents, solution retarders and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerol, glycerine-formal, tetrahydrofurfuryl alcohol, polyethylene glycols and fatty acid esters of sorbitan or mixtures of these substances.

For parenteral administration, the solutions and emulsions can also be in a sterile form which is isotonic with blood.

Suspensions can contain the customary excipients in addition to the active compound or compounds, such as liquid diluents, for example water, ethyl alcohol, propyl alcohol, suspending agents, for example ethoxylated isostearyl alcohols, polyoxyethylene sorbitol and sorbitan esters, microcrystalline cellulose, aluminium metahydroxide, bentonite, agar-agar and tragacanth or mixtures of these substances.

The formulation forms mentioned can also contain dyestuffs, preservatives and additives which improve the odour and flavour, for example peppermint oil and eucalyptus oil, and sweeteners, for example saccharin.

The therapeutically active compounds should preferably be present in the abovementioned pharmaceutical preparations in a concentration of about 0.1 to 99.5, preferably 0.5 to 95, % by weight of the total mixture.

The abovementioned pharmaceutical preparations can also contain other pharmaceutical active compounds in addition to the active compounds according to the invention.

The abovementioned pharmaceutical preparations are manufactured in the usual manner according to known methods, for example by mixing the active compound or compounds with the excipient or excipients.

The present invention also includes the use of the active compounds according to the invention, and of pharmaceutical preparations which contain one or more active compounds according to the invention in medicine for the treatment of the abovementioned illnesses.

The active compounds or the pharmaceutical preparations can be administered topically, orally, parenterally, intraperitoneally and/or rectally, preferably parenterally, and especially intravenously.

In general it has proved advantageous in medicine to administer the active compound or compounds in amounts of about 2.5 to about 200, preferably 5 to 150, mg/kg of body weight every 24 hours, optionally in the form of several individual administrations, in order to achieve the desired results.

However, it can be necessary to deviate from the dosages mentioned and in particular to do so as a function of the nature and body weight of the subject to be treated, the nature and severity of the illness, the nature of the preparation and of the administration of the medicine, and the time or interval over which the administration takes place. Thus it can suffice in some cases to manage with less than the abovementioned amount of active compound whilst in other cases the abovementioned amount of active compound must be exceeded. The particular required optimum dosage and the type of administration of the active compounds can easily be decided by anyone skilled in the art, on the basis of his expert knowledge.

PREPARATION EXAMPLES

Example (Ia-1)

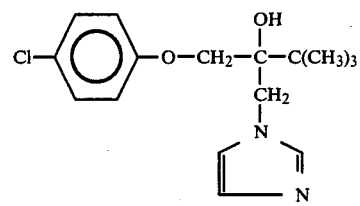

8.02 g (0.1178 mole) of imidazole are added to 2.71 g (0.1178 mole) of sodium in 250 ml of absolute ethanol. A solution of 14.17 g (0.0589 mole) of 2-(4-chlorophenoxymethyl)-2-tert.-butyl-oxirane in 100 ml of ethanol is added dropwise at room temperature within 30 minutes. The reaction mixture is then heated under reflux for 8 hours, evaporated and the residue is taken up in ether. The mixture is extracted three times with 1N hydrochloric acid, and the combined hydrochloric acid phases are neutralised with sodium bicarbonate and then extracted with ethyl acetate. After evaporation and recrystallisation from cyclohexane, 11.6 g (64% of theory) of 2-(4-chlorophenoxymethyl)-3,3-dimethyl-1-(imidazol-1-yl)-2-butanol of melting point 154°–155° C. are obtained.

Preparation of the starting material

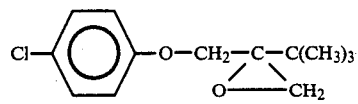

A solution of 162 ml (2.2 mole) of dimethyl sulphide in 400 ml of absolute acetonitrile is added to a solution of 189 ml (2.0 mole) of dimethyl sulphate in 1,200 ml of absolute acetonitrile at room temperature. The reaction mixture is allowed to stir overnight at room temperature. Then 118.8 g (2.2 mole) of sodium methylate are added. The mixture is allowed to stir for 30 minutes and then a solution of 272 g (1.2 mole) of 1-(4-chlorophenoxy)-3,3-dimethyl-2-butanone in 600 ml of absolute acetonitrile is added dropwise within 30 minutes. The reaction mixture is allowed to stir overnight. It is then evaporated, and the residue is partitioned between water and ethyl acetate, the organic phase is separated off, washed twice with water and once with saturated sodium chloride solution, dried over sodium sulphate, evaporated and the residue is distilled in vacuo. 242.2 g (84% of theory) of 2-(4-chlorophenoxymethyl)-2-tert.-butyl-oxirane of boiling point 115°–22° C./0.003 mm Hg column and of melting point 50°–52° C. are obtained.

Example (Ia-2)

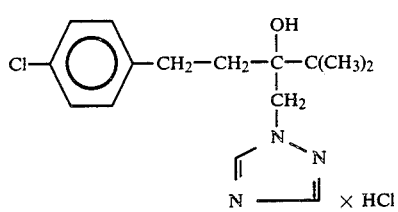

A solution of 17.9 g (0.075 mole) of 2-(4-chlorophenylethyl)-2-tert.-butyloxirane and 6.9 g (0.1 mole) of 1,2,4-triazole in 30 ml of ethanol in a sealed tube is heated at 150° C. for 20 hours. The tube is allowed to cool and the reaction solution is evaporated. The residue is dissolved in ether, washed three times with water and once with sodium chloride solution, dried over sodium sulphate and evaporated. The residue is chromatographed over a column of silican gel (mobile phase: dichloroethane/ethyl acetate 1:1). 12.3 g (53.2% of theory) of 1-(4-chlorophenyl)-4,4-dimethyl-3-(1,2,4-triazol-1-yl-methyl)-3-pentanol are obtained as a viscous oil.

The hydrochloride of melting point 212° C. is obtained in virtually quantitative yield by customary reaction with ethereal hydrogen chloride.

The following compounds of the formula (Ia)

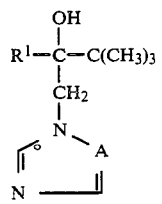

are obtained in a corresponding manner:

| Example No. | R¹ | A | Melting point (°C.) |
|---|---|---|---|
| Ia-3 | ⌬-⌬-O—CH₂— | CH | 169–70.5 |
| Ia-4 | ⌬-⌬-O—CH₂— | N | 118–19.5 |
| Ia-5 | Cl-⌬(CH₃)-O—CH₂— | N | 125.5–29 |
| Ia-6 | Cl-⌬(Cl)-O—CH₂— | N | 120.5–23.5 |
| Ia-7 | F-⌬-CH₂—CH₂— | N | 91–95.5 |
| Ia-8 | Cl-⌬(Cl)-O—CH₂— | CH | 152–54 |
| Ia-9 | Cl-⌬(CH₃)-O—CH₂— | CH | 157–59 |
| Ia-10 | Cl-⌬-CH₂—CH₂— | CH | 157.5–59.5 |
| Ia-11 | F-⌬-CH₂—CH₂— | CH | 124–25 |
| Ia-12 | Cl-⌬(Cl)-CH₂—CH₂— | CH | 118–19 |
| Ia-13 | Cl-⌬(Cl)-CH₂—CH₂— | N | 94–95 |
| Ia-14 | F-⌬-O—CH₂— | CH | 141–42 |
| Ia-15 | F-⌬-O—CH₂— | N | 73–75 |
| Ia-16 | Cl-⌬-O—CH₂— | CH | 124 |
| Ia-17 | F-⌬(Cl)-O—CH₂— | CH | 137 |
| Ia-18 | F-⌬(Cl)-O—CH₂— | N | 130 |
| Ia-19 | Cl-⌬-⌬-O—CH₂— | CH | 174–76 |
| Ia-20 | Cl-⌬-⌬-O—CH₂— | N | 109–11 |
| Ia-21 | CH₃O-⌬-O—CH₂— | N | 63–66 |
| Ia-22 | F₃CO-⌬-O—CH₂— | N | $n_D^{20} = 1.4902$ |
| Ia-23 | Cl-⌬-CH=CH— | N | 115–117 |
| Ia-24 | CH₃-⌬(CH₃)(CH₃)-O—CH₂— | N | 75–76.5 |

-continued

| Example No. | R¹ | A | Melting point (°C.) |
|---|---|---|---|
| Ia-25 | 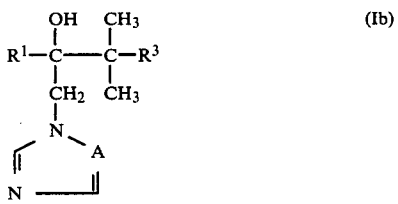 | N | 102–103.5 |
| Ia-26 | Cl—⌬—O—CH₂— (with CH₃ groups ortho); naphthyl-O—CH₂— | N | 128.5–131 |

The following compounds of the formula (Ib)

$$R^1-\underset{\underset{CH_2}{|}}{\overset{\overset{OH}{|}}{C}}-\underset{\underset{CH_3}{|}}{\overset{\overset{CH_3}{|}}{C}}-R^3$$
$$\underset{N}{\overset{|}{\underset{\parallel}{N}}}\underset{\phantom{N}}{\overset{A}{\diagdown\phantom{N}}}$$

(Ib)

are obtained in a manner corresponding to Examples Ia-1 and Ia-2:

| Example No. | R¹ | R³ | A | Melting point (°C.) or $n_D^{20}$ |
|---|---|---|---|---|
| Ib-1 | Cl—⌬—O—CH₂— | —O—⌬—⌬ | N | resin |
| Ib-2 | ⌬—⌬—O—CH₂— | —O—⌬—Cl | N | resin |
| Ib-3 | Cl—⌬—O—CH₂ | —O—⌬—Cl | N | resin |
| Ib-4 | F—⌬—O—CH₂— | —O—⌬—Cl | N | resin |
| Ib-5 | Cl—⌬(Cl)—O—CH₂— | —O—⌬—Cl | N | resin |
| Ib-6 | Cl—⌬(Cl)—O—CH₂— | —O—⌬ | N | resin |

Example Ic-1

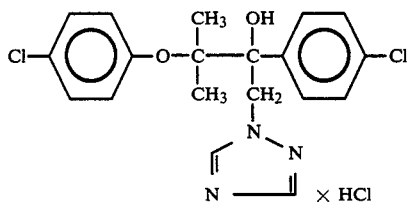

A solution of 30 g (0.093 mole) of 2-(4-chlorophenyl)-2-[2-(p-chlorophenoxy)-2-propyl]oxirane in 40 ml of n-propanol is added dropwise, at room temperature, to a solution of 7.6 g (0.107 mole) of 1,2,4-triazole-sodium in 60 ml of n-propanol. The reaction mixture is allowed to stir at reflux temperature for 48 hours, then cooled, water is added and the mixture is extracted with methylene chloride. The organic phase is dried over sodium sulphate and evaporated in vacuo. The oily residue is purified by column chromatography. 6.7 g (18.4% of theory) of 3-(4-chlorophenoxy)-2-(4-chlorophenyl)-3-methyl-1-(1,2,4-triazol-1-yl)-2-butanol are obtained. This is vigorously stirred with 20 ml of saturated hydrogen chloride/ether solution at room temperature. The precipitate which separates out is filtered off with suction, washed with a little ether and dried in vacuo at 40° C. 6.5 g (89% of theory relative to base employed) of 3-(4-chlorophenoxy)-2-(4-chlorophenyl)-3-methyl-1-(1,2,4-triazol-1-yl)-2-butanol hydrochloride of melting point 135° C. are obtained.

Preparation of the starting material

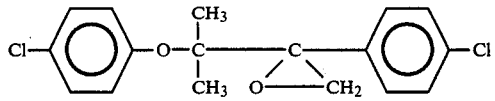

A solution of 59.2 g (0.47 mole) of dimethyl sulphate and 32 g (0.517 mole) of dimethyl sulphide in 270 ml of acetonitrile is allowed to stir at room temperature for 5 days. Then, at 20° to 25° C., a solution of 87 g of 4-chlorophenyl 2-(p-chlorophenoxy)-2-propyl ketone in 80 ml of acetonitrile is added dropwise within about 2 hours. At the same temperature, 28.7 g (0.53 mole) of sodium methylate are added, the mixture is allowed to stir for 12 hours and then evaporated. The residue is vigorously stirred with a mixture of 200 ml of ethyl acetate and 150 ml of water overnight. The organic phase is separated off, dried over sodium sulphate and evaporated in vacuo. 49 g (76% of theory) of crude 2-(4-chlorophenyl)-2-[2-(p-chlorophenoxy)-2-propyl]oxirane are obtained, and this is immediately reacted further.

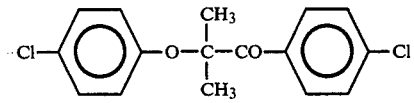

52 g (0.3982 mole) of p-chlorophenol and 55 g (0.3982 mole) of potassium carbonate in 400 ml of toluene are heated under reflux with a water separator for 2 hours. The mixture is cooled to 40° C. and a solution of 2-bromo-2-propyl 4-chlorophenyl ketone in 170 ml of toluene is added dropwise.

This reaction mixture is allowed to stir at 100° C. for 5 hours, then cooled, water is added and the organic phase is separated off. The latter is washed with dilute sodium hydroxide solution and water, dried over sodium sulphate and evaporated. 87 g (85% of theory) of crude 4-chlorophenyl 2-(p-chlorophenoxy)-2-propyl ketone are obtained, which is immediately reacted further.

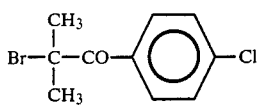

1 ml of hydrogen bromide/glacial acetic acid is added to 65.5 g (0.36 mole) of 4-chlorophenyl isopropyl ketone in 200 ml of chloroform and then 57.5 g (0.36 mole) of bromine is added dropwise at 30° C. The mixture is allowed to stir at room temperature for 30 minutes and then evaporated in vacuo. 86.6 g (92% of theory) of crude 2-bromo-2-propyl 4-chlorophenyl ketone are obtained, which is immediately reacted further.

The following compounds of the formula (Ic)

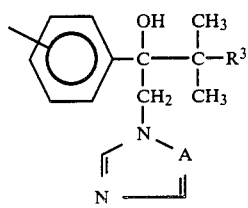

are obtained in a corresponding manner:

| Example No. | ⟨◯⟩— | $R^3$ | A | Melting point (°C.) |
|---|---|---|---|---|
| Ic-2 | F—⟨◯⟩— | —O—⟨◯⟩—Cl | N | 82 |
| Ic-3 | Cl—⟨◯⟩— | —O—⟨◯⟩(Cl)—Cl | CH | 80–82 |
| Ic-4 | Cl—⟨◯⟩— | —O—⟨◯⟩(Cl)—Cl | N | 96–98 |
| Ic-5 | Cl—⟨◯⟩— | —O—⟨◯⟩(Cl) | N | 114–16 |
| Ic-6 | Cl—⟨◯⟩— | —O—⟨◯⟩(Cl) | CH | 194 |
| Ic-7 | Cl—⟨◯⟩— | —O—⟨◯⟩(CH3)—Cl | N | 117 |
| Ic-8 | Cl—⟨◯⟩— | —O—⟨◯⟩—CH3 | N | 62 |
| Ic-9 | Cl—⟨◯⟩— | —O—⟨◯⟩—CH3 | CH | 106 |
| Ic-10 | F—⟨◯⟩— | —O—⟨◯⟩—F | N | 78 |
| Ic-11 | F—⟨◯⟩— | —O—⟨◯⟩—Cl | CH | 154 |
| Ic-12 | F—⟨◯⟩— | —O—⟨◯⟩—F | CH | 178 |
| Ic-13 | F—⟨◯⟩— | —O—⟨◯⟩(F) | N | 120 |
| Ic-14 | F—⟨◯⟩— | —O—⟨◯⟩(Cl) | N | 147 |

Example (Id-1)

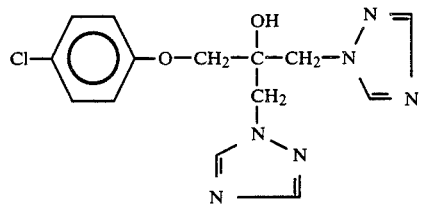

9.4 g (0.04 mole) of 2-chloromethyl-2-(4-chlorophenoxymethyl)oxirane are added dropwise to a mixture of 13.6 g (0.2 mole) of 1,2,4-triazole and 13.8 g (0.1 mole) of potassium carbonate in 200 ml of acetone with stirring. The mixture is allowed to stir at room temperature for 15 hours and then under reflux for 22 hours. The reaction mixture is then filtered cold and the filtrate is evaporated in vacuo. The oily residue is dissolved in chloroform, and the solution is washed with water, dried over sodium sulphate and purified by chromatography (silica gel 60, Merck, chloroform/methanol=20:1). 5.8 g (43%) of theory) of 2-(4-chlorophenoxymethyl)-1,3-di(1,2,4-triazol-1-yl)-2-hydroxypropane of melting point 99° C. are obtained.

Preparation of the starting material

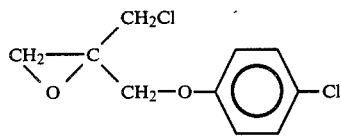

12.85 g (0.1 mole) of 4-chlorophenol in 50 ml of acetone are added dropwise to a mixture of 14.1 g (0.1 mole) of 2,2-di(chloromethyl)oxirane and 13.8 g (0.1 mole) of potassium carbonate in 200 ml of acetone. The mixture is heated under reflux for 18 hours, allowed to cool and filtered. The filtrate is evaporated in vacuo, the residue is dissolved in chloroform, and the solution is washed with water, dried over sodium sulphate and evaporated. After purification by distillation, 7.6 g (32.5% of theory) of 2-chloromethyl-2-(4-chlorophenoxymethyl)oxirane of boiling point 150° C./0.5 mbar are obtained.

The following compounds of the formula (Id)

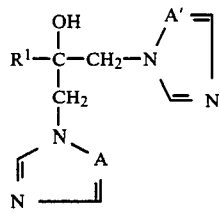

(Id)

can be obtained in a corresponding manner:

| Example No. | R¹ | A | A' | Melting point (°C.) |
|---|---|---|---|---|
| Id-2 | C₆H₅—C₆H₄—O—CH₂— | N | N | 140 |
| Id-3 | 2,4-Cl₂—C₆H₃—O—CH₂— | N | N | 138 |
| Id-4 | 2-Cl—C₆H₄—O—CH₂— | N | N | 95 |
| Id-5 | 2,6-Cl₂—C₆H₃—O—CH₂— | N | N | 166 |
| Id-6 | 4-F—C₆H₄—O—CH₂— | N | N | 90 |
| Id-7 | 2,5-Cl₂—C₆H₃—O—CH₂— | N | N | 130 |
| Id-8 | 4-Cl—C₆H₄—O—CH₂— | CH | CH | 100 |
| Id-9 | 3,4-Cl₂—C₆H₃—O—CH₂— | N | N | 158 |
| Id-10 | 4-CH₃O—C₆H₄—O—CH₂— | N | N | 118 |
| Id-11 | 4-CH₃S-3-CH₃—C₆H₃—O—CH₂— | N | N | 70 |
| Id-12 | 3,5-Cl₂—C₆H₃—O—CH₂— | N | N | 162 |
| Id-13 | 4-(CH₃)₃C—C₆H₄—O—CH₂— | N | N | 98 |
| Id-14 | 4-Cl—C₆H₄—C₆H₄—O—CH₂— | N | N | 166 |

Example (Ie-1)

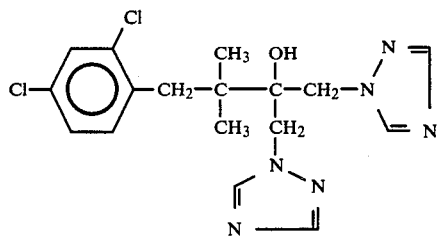

3.7 g (52.6 mmol) of 1,2,4-triazole are added, with stirring, to a solution of 0.11 g (47 mmol) of sodium in 30 ml of n-propanol at room temperature. The mixture is heated to reflux temperature and a solution of 15.4 g (47 mmol) of 2-(2,4-dichlorophenyl-tert.-butyl)-2-(1,2,4-triazol-1-ylmethyl)oxirane in 20 ml of n-propanol is added. The reaction mixture is heated under reflux for 15 hours, then cooled and added to water. The mixture is extracted with methylenechloride, and the organic phase is dried over sodium sulphate and evaporated. The residue is purified by column chromatography (silica gel; ethyl acetate:cyclohexane=3:1). 3.5 g (18.8% of theory) of 4-(2,4-dichlorophenyl)-3,3-dimethyl-2-(1,2,4-triazol-1-ylmethyl)-1-(1,2,4-triazol-1-yl)-2-butanol of melting point 126° C. are obtained.

Preparation of the starting material

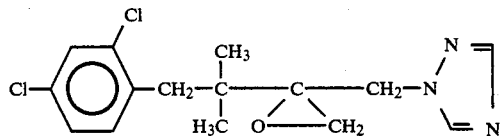

15.7 g (71.2 mmol) of trimethylsulphonium iodide are dissolved in 16 g of dimethyl sulphoxide under an atmosphere of nitrogen. 9.4 g (71.2 mmol) of potassium tert.-butylate are added at room temperature, with cooling. The mixture is allowed to stir for 6 hours and then a solution of 20 g (64.1 mmol) of 4-(2,4-dichlorophenyl)-3,3-dimethyl-1-(1,2,4-triazol-1-yl)butanone in 30 ml of tetrahydrofuran is added. The reaction mixture is allowed to stir at room temperature for 15 hours and under reflux for 4 hours, then cooled and poured into water. The mixture is extracted with methylene chloride, and the organic phase is dried over sodium sulphate and evaporated in vacuo. 15.4 g (73.7% of theory) of 2-(2,4-dichlorophenyl-tert.-butyl)-2-(1,2,4-triazol-1-ylmethyl)oxirane of refractive index $n_D^{20}=1.5539$ are obtained.

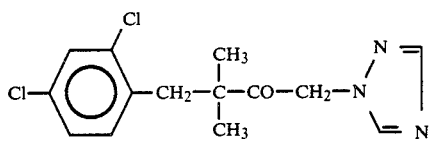

30 g (0.09 mole) of 1-bromo-4-(2,4-dichlorophenyl)-3,3-dimethyl-2-butanone, 12.4 g (0.18 mole) of 1,2,4-triazole and 24.8 g (0.18 mole) of potassium carbonate in 300 ml of acetone are heated under reflux for 6 hours. The mixture is then allowed to cool, the solid is filtered off with suction and the mother liquor is evaporated in vacuo. The residue is taken up in methylene chloride, and the solution is washed with water, dried over sodium sulphate and evaporated in vacuo. The residue is recrystallised from diethyl ether. 12.8 g (45.6% of theory) of 4-(2,4-dichlorophenyl)-3,3-dimethyl-1-(1,2,4-triazol-1-yl)-2-butanone of melting point 85° C. are obtained.

The following compounds of the formula (Ie)

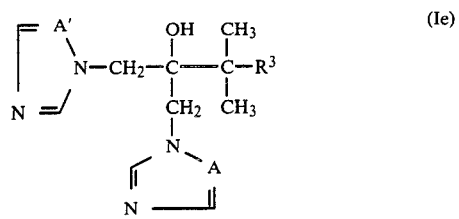

are obtained in a corresponding manner:

| Example No. | R³ | A | A' | Melting (°C.) |
|---|---|---|---|---|
| Ie-2 | Cl—⟨O⟩—CH₂— | N | N | 132 |
| Ie-3 | CH₃—⟨O⟩—CH₂— | N | N | 124 |
| Ie-4 | Cl—⟨O⟩—CH₂— | N | CH | >220 (×HCl) |
| Ie-5 | F—⟨O⟩—CH₂— | N | N | 129 |

It is true that it has already been disclosed that certain benzimidazole derivatives, such as, in particular, 2-(α-hydroxybenzyl)-benzimidazole show antiviral properties in cell cultures. However, these compounds are only weakly active or are inactive in experimental animals (compare Chemotherapy of Virus Diseases, Vol. I., pages 115 to 179, 1972). Moreover, the action of these compounds is only directed against picornaviruses. Thus the substances have achieved no significance as an antiviral agent in pharmacy. In contrast, the compounds according to the invention have an excellent antiviral action, as is shown by the experimental results below.

Example A

Cell culture experiment/plaque reduction test

The plaque reduction test was carried out by the method of Herrmann et al. (Proc. Soc. Exp. Biol. Med. 103, 625–628 (1960). Mouse L-929 cells were spread on Petri dishes.

Each Petri dish contains between 1 and $2.5 \times 10^6$ cells. For the infection, the culture medium was removed. The cells were infected by 1 ml of a virus suspension which contains $5 \times 10^3$ plaque-forming units an the test substance in a non-cyctotoxic concentration.

After an adsorption time of one hour, the virus solution was removed and 5 ml of covering medium containing test substance were added to each Petri dish.

After 3–4 days, the cells were stained and the virus plaques were counted.

The number of plaques which form after infection of cells with herpes simplex virus is less in cells infected and treated with compounds according to the invention than in infected and untreated cells (compare Table A).

TABLE A

Cell culture experiment/treatment of L-929 cells which have been infected with herpes simplex virus.

| Compound according to Preparation Example No. | Antiviral action in cell culture |
|---|---|
| Ia-1 | + |
| Ia-3 | ++ |
| Ia-4 | ++ |
| Ic-1 | + |
| Ic-2 | + |
| Id-1 | + |
| Id-2 | + |
| Ie-2 | + |

++ = % plaque reduction greater than 50%
+ = % plaque reduction less than 30%

Example B

Animal experiment/cutaneous test on guinea pigs

The test carried out was derived from the method worked out by Hubler et al. (J.Invest. Dermatol. 62, 92–95, (1974)). Guinea pigs weighing 500 to 600 g were depilated on the abdomen and anaesthetised with nembutal (15 mg/kg i.p.). Previously marked areas of skin were infected with a multiple vaccination lancet ('vaccination gun'). The virus material used was medium from rabbit kidney cells which had been infected with type I herpes simplex virus. Treatment can be topical, parenteral, oral, intraperitoneal or intravenous. The controls used were infected animals which were untreated or treated with placebo. The evaluation used the number and size of the herpes vesicles. The results are compiled in the table below.

TABLE B

Animal experiment/cutaneous test on guinea pigs

| Compound according to Preparation Example | Antiviral action in the cutaneous test (guinea pigs) | |
|---|---|---|
| | p.o. treatment | topical treatment |
| Ia-2 | + | ++ |
| Ia-3 | ++ | ++ |
| Ia-4 | ++ | ++ |
| Ib-1 | + | not tested |
| Ib-2 | + | not tested |
| Id-2 | + | not tested |

++ = > 50% reduction in number and size of the herpes vesicles
+ = < 50% reduction in the number and size of the herpes vesicles

We claim:

1. Method of combatting virus infections, which comprises administering to a warm-blooded animal requiring antiviral treatment, an antivirally effective amount of a hydroxyethylazolyl derivative of the formula

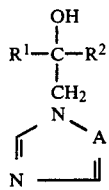

in which
- A represents a nitrogen atom or the CH group,
- $R^1$ represents phenyl, phenoxymethyl, phenethyl or phenethyl, each of which is optionally substituted in the benzenoid moiety by halogen, alkyl having 1 to 4 carbon atoms, alkoxy or alkylthio, each having 1 to 2 carbon atoms, halogenoalkyl and halogenoalkoxy, and halogenoalkylthio each having 1 to 2 carbon atoms with 1 to 5 identical or different fluorine or chlorine atoms, phenyl or halogenophenyl or represents naphthyloxymethyl, 1,2,4-triazol-1-ylmethyl or imidazol-1-ylmethyl,
- represents the group —$C(CH_3)_2$—$R^3$, 1,2,4-triazol-1-ylmethyl or imidazol-1-methyl and
- $R^3$ represents methyl or phenoxy or benzyl, both of which are optionally substituted by substituents defined for $R^1$ above, with the proviso that A does not represent a nitrogen atom at the same time as $R^1$ represents a p-chlorophenoxymethyl and $R^2$ represents tert.-butyl, and/or their physiologically tolerated acid addition salts.

2. Method of claim 1 wherein the hydroxyethylazolyl derivative is of the formula (I) in claim 1, in which
- A and $R^3$ have the meaning given in claim 1, and
- $R^1$ represents phenoxymethyl, phenethyl or phenethenyl, each of which optionally has 1 to 3 identical or different substituents in the phenyl moiety, said substituents being: fluorine, chlorine, methyl, trifluoromethyl, trifluoromethoxy, trifluoromethylthio, phenyl and chlorophenyl; or represents naphthyloxymethyl; and
- $R^2$ represents tert.-butyl, which at the same time A does not represent a nitrogen atom and $R^1$ does not represent p-chlorophenoxy;

and/or their physiologically tolerated acid addition salts.

3. Method of claim 1 wherein the hydroxyethylazolyl derivative is of the formula (I) in claim 1, in which
- A has the meaning indicated in claim 1, and
- $R^1$ represents phenyl which optionally has one or two identical or different substituents, said substituents being the phenyl substituents identified above defining $R^1$; and
- $R^2$ represents the group —$C(CH_3)$—$_2$—$R^3$, while
- $R^3$ represents phenoxy which optionally has one or two identical or different substituents, said substituents being the phenyl substituents already mentioned above defining $R^1$, and/or their physiologically tolerated acid addition salts.

4. Method of claim 1 wherein the hydroxyethylazolyl derivative is of the formula (I) in claim 1 in which
- A and $R^3$ have the meaning indicated in claim 1 and
- $R^1$ represents phenoxymethyl which optionally has one or two identical or different substituents in the phenyl moiety, said substituents being the phenyl substituents identified above defining $R^1$; and
- $R^2$ represents 1,2,4-triazol-1-ylmethyl or imidazol-1-ylmethyl, and/or their physiologically tolerated acid addition salts.

5. Method of claim 1 wherein the hydroxyethylazolyl derivative is of the formula (I) in claim 1, in which
- A has the meaning given in claim 1 and
- $R^1$ represents 1,2,4-triazol-1-ylmethyl or imidazol-1-ylmethyl; and
- $R^2$ represents the group —$C(CH_3)_2$—$R^3$, while
- $R^3$ represents benzyl which optionally has one or two identical or different substituents, said benzenoid substituents being the benzenoid substituents identified above defining $R^1$, and their physiologically tolerated acid addition salts.

6. Method of claim 1 wherein the hydroxyethylazolyl derivative is 1-(4-chlorophenyl)-4,4-dimethyl-3-(1,2,4-triazol-1-ylmethyl)-3-pentanol.

7. Method of claim 1 wherein the hydroxyethylazolyl derivative is 1-(4-phenylphenyl)oxymethyl-3,3-dimethyl-2-(1,2,4-triazol-1-yl)-2-butanol.

8. Method of claim 1 wherein the hydroxyethylazolyl derivative is 1-(4-phenylphenyl)oxymethyl-3,3-dimethyl-2-(imidazol-1-yl)-2-butanol.

* * * * *

UNITED STATES PATENT AND TRADEMARK OFFICE
CERTIFICATE OF CORRECTION

PATENT NO. : 4,668,660

DATED : May 26, 1987

INVENTOR(S) : Arnold Paessens, et al.

It is certified that error appears in the above-identified patent and that said Letters Patent is hereby corrected as shown below:

| | |
|---|---|
| Title Page, under "Foreign Patent Documents", line 2 | Delete "European Pat. Off." and substitute --Fed. Rep. of Germany-- |
| Col. 7, line 22 | Delete "silican" and substitute --silica-- |
| Col. 9, line 40, Ex. No. 1b-3, line 3 under "$R^1$" | End of formula delete "$CH_2$" and substitute --$CH_2-$-- |
| Col. 14, line 33 | Delete "methylenechloride" and substitute --methylene chloride-- |
| Col. 15, line 35 | After "Melting" insert --point-- |
| Col. 16, line 6 | Delete "an" and substitute --and-- |
| Col. 17, line 14 | Before ", each" delete "phenethyl" and substitute --phenethenyl-- |
| Col. 17, line 24 | Before "represents" insert --$R^2$-- |

Signed and Sealed this

Twenty-ninth Day of March, 1988

Attest:

DONALD J. QUIGG

Attesting Officer

Commissioner of Patents and Trademarks